US00PP19235P2

(12) United States Plant Patent
Hambali

(10) Patent No.: US PP19,235 P2
(45) Date of Patent: Sep. 16, 2008

(54) ***AGLAONEMA* PLANT NAMED 'TWYAG0013'**

(50) Latin Name: *Aglaonema rotundum×A. costatum hybrid*
Varietal Denomination: TWYAG0013

(75) Inventor: Gregori Garnadi Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/973,749

(22) Filed: Oct. 10, 2007

(51) Int. Cl.
*A01H 5/00* (2006.01)

(52) U.S. Cl. ..... Plt./376
(58) Field of Classification Search ..... Plt./376
See application file for complete search history.

*Primary Examiner*—Annette H Para
(74) *Attorney, Agent, or Firm*—Jondle & Associates, P.C.

(57) ABSTRACT

A new *Aglaonema* plant particularly distinguished by a small stature, dense leafy, compact, full and mounded growth habit, green leaves with pink blotches, profuse suckering, consistent progressive growth and produces numerous axillary branches and leaves, is disclosed.

1 Drawing Sheet

Genus and species: *Aglaonema rotundum×A. costatum hybrid.*
Variety denomination: 'TWYAG0013'.

BACKGROUND OF THE NEW PLANT

The present invention comprises a new and distinct cultivar of *Aglaonema,* botanically known as *Aglaonema rotundum×A. costatum* hybrid, and hereinafter referred to by the cultivar name 'TWYAG0013'. The new cultivar originated from a hybridization made in 2000 in Bogor, Indonesia. The female parent was an unknown individual plant of *A. rotundum* (patent status unknown), while the male parent was an unknown individual plant of *A. costatum* (patent status unknown). A single plant was chosen for further selection in February 2002.

The new cultivar was created in Bogor, Indonesia and has been asexually reproduced repeatedly by vegetative cuttings, and sucker division in Apopka, Fla. and Bogor, Indonesia over a 5-year period. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla. and Bogor, Indonesia.

1. Small in stature;
2. Densely leafy, compact, full and mounded growth habit;
3. Green leaves with pink blotches;
4. Profuse suckering;
5. Consistent progressive growth; and
6. Produces numerous axillary branches and leaves.

DESCRIPTION OF THE PHOTOGRAPH

This new *Aglaonema* plant is illustrated by the accompanying photograph which shows overall plant habit. The colors shown are as true as can be reasonably obtained by conventional photographic procedures.

DESCRIPTION OF THE NEW CULTIVAR

The following detailed description sets forth the distinctive characteristics of 'TWYAG0013'. The data which defines these characteristics were collected from asexual reproductions carried out in Apopka, Fla. The plant history was taken on 6-month old plants started from a single 4-leaf rooted cutting, still in a vegetative state and grown in Apopka, Fla. Rooted cuttings were planted in 15-cm pots and grown in a greenhouse in August 2006. The average daily temperature was about 85° to 95° F. and the average nightly temperature was about 72° to 78° F. Color readings were taken under natural light. Color references are primarily to the RHS Colour Chart of The Royal Horticultural Society of London (RHS) (2001).

DETAILED BOTANICAL DESCRIPTION

Classification:
- *Family.*—Araceae.
- *Botanical.*—*Aglaonema* hybrid.
- *Common name.*—Chinese Evergreen.

Parentage: The female parent is an unknown individual plant of *A. rotundum* and the male parent is an unknown individual plant of *A. costatum.*

Growth:
- *Form.*—Wider than tall; new leaves emerge straight upright, mature leaves lean outward.
- *Growth and branching habit.*—Small, compact, densely leafy, mounded growth habit; small in stature with basal branching.
- *Height* (*from soil to top of leaf plane*).—17 cm to 23 cm.
- *Diameter* (*area of spread, measured from leaf tip to leaf tip across the canopy*).—35 cm to 38 cm.
- *Time to produce a finished flowering plant.*—6-months starting from a single 4-leaf rooted cutting.

*Vigor.*—Consistent progressive growth resulting in plants which produce numerous axillary branches and leaves.

*Growth rate.*—Somewhat slower than typical commercial *Aglaonema* cultivars.

*Root description.*—Thick, fleshy white roots with finer lateral branches.

*Durability of foliage to stresses.*—Leaves hold up well against damage from shipping and handling; plant is durable, excellent indoor keeping quality.

*High temperature tolerance.*—To about 104° F. for several hours without damage.

*Lower temperature tolerance.*—To about 55° F. for several hours without damage.

Stems:

*Number of branches per plant.*—6.

*Length* (*from soil line to the junction of the newest two leaves*).—7 cm to 9 cm.

*Diameter* (*measured from the midpoint*).—0.9 cm.

*Internode length.*—0.5 cm to 0.8 cm.

*Color.*—Immature: RHS 146B to RHS 146C tinged with RHS 145C. Mature: RHS 146B. Oldest stems: RHS 147A and RHS 146A tinged with RHS 164B to RHS 164C.

*Appearance* (*shape*).—Columnar, cylindrical upright.

*Aspect.*—Vertical, upright, or leaning outward about 30°–40°; apex of stem often upturned.

*Strength.*—Sturdy, somewhat flexible.

*Axillary buds.*—Shape: Elliptic to ovate, flat to convex. Length: 0.35 cm. Width: 0.20 cm. Color: RHS 146C to RHS 145C.

Leaves:

*Arrangement.*—Alternate, single, simple, oriented opposite along the stem.

*Quantity of leaves per stem.*—6.

*Immature leaf* (*New expanded leaf*).—Color: Upper surface: Base color darker and greener than, but closet to RHS 147A; marked with spots and coalescing blotches of RHS 155D, RHS 155D tinged with RHS 56D, and RHS 56B to RHS 56C. Lower surface: RHS 147A tinged with RHS 50C base color; upper surface pattern and markings visible through the lower surface; leaf blade marked with spots and coalescing blotches of RHS 50C to RHS 50D.

*Mature leaf.*—Color: Upper surface: Base color darker and greener than but closet to RHS 147A marked with spots and coalescing blotches of RHS 54D, and RHS 56A to RHS 56B. Lower surface: Base color RHS 147A tinged with RHS 54C; upper surface pattern and marking visible through the lower surface; leaf blade marked with spots and coalescing blotches of RHS 54B to RHS 54C.

*Length.*—12.0 cm to 15.0 cm.

*Width.*—Flattened: 10.5 cm to 11.5 cm. Not flattened (natural): 8.5 cm to 10.2 cm.

*Shape.*—Ovate.

*Apex.*—Acute to cuspidate.

*Base.*—Cordate to obtuse.

*Margin.*—Smooth, entire, with some broad undulations.

*Texture.*—Smooth, leathery; immature leaves shiny; mature leaves glossy to dull; the leaf blade is convex between the main veins resulting in a textured appearance.

*Pubescence.*—None.

*Venation pattern.*—Pinnate, radiating outward from the midrib in a herringbone arrangement.

*Venation color* (*Immature leaf*).—Upper surface: Primary veins: RHS 155D tinged with RHS 56D. Midrib-proximal: RHS 155C to RHS 155D. Midrib-distal: RHS 56B to RHS 56C. Lower surface: Primary veins: RHS 50C and RHS 50D. Midrib-proximal: RHS 147D streaked with RHS 147B. Midrib-distal: RHS 50C to RHS 50D.

*Venation color* (*Mature leaf*).—Upper surface: Primary veins: RHS 155 D tinged with RHS 56A to RHS 56B. Midrib-proximal: RHS 155C. Midrib-distal: RHS 155C tinged with RHS 56A. Lower surface: Primary veins: RHS 155D tinged with RHS 54C to RHS 54D. Midrib-proximal: RHS 147D streaked with RHS 147B. Midrib-distal: RHS 54B to RHS 54C.

*Petioles.*—Aspect: Vertical upright when newly expanded, becoming curved outward and about 30° with maturity. Length: 5.8 cm to 6.6 cm. Diameter: Distal: 0.35 cm. Proximal (petiole and petiole sheath clasps the stem proximally); Flattened (width): 2.7 cm. Natural diameter: 0.9 cm. Depth: 0.9 cm. Color: Distal: RHS 147A (between the top of the wing and the base of the leaf). Proximal: RHS 147A to RHS 147B. Area adjacent to stem: RHS 146C to RHS 146D tinged with RHS 164D. Wing length: 3.3 cm to 4.4 cm. Wing diameter: Mid-point: 0.8 cm. Base: 0.9 cm. Depth: 0.9 cm. Wing color: Inside: RHS 155C and RHS 147C. Outside: RHS 147A to RHS 147B. Area adjacent to stem: RHS 146C to RHS 146D tinged with RHS 164D.

*Cataphylls.*—Length: 4.0 cm to 4.9 cm. Width: 1.8 cm to 2.2 cm. Shape: Lanceolate, keeled, translucent. Base: Clasping the stem. Tip: Cuspidate.

*Color.*—Inside distal: RHS 146B to RHS 146C, keel tinged with RHS 49D. Inside proximal: RHS 145D. Outside distal: RHS 147B, keel tinged with RHS 49C to RHS 49D. Outside proximal: RHS 147C to RHS 147D.

Inflorescence:

*Arrangement.*—1 inflorescences per stem, persistent; hooded flower spathes surrounding a columnar spadix borne atop an upright peduncle; the spadix is a central column of sessile, simple male and female flowers separated into two zones, the male flowers occupy the upper three-fours of the spadix while the female flowers occupy the lower one-fourth of the spadix.

*Aspect.*—Upright.

*Height* (*from base of peduncle to tip of spathe*).—10.5 cm.

*Diameter/width.*—1.3 cm.

*Flowering habit.*—Seasonal, summer and fall as observed in Apopka, Fla.

*Number of inflorescences per plant.*—2.

*Fragrance.*—None.

*Ratio of inflorescence opening.*—About 1 new flower every 14–21 days.

*Peduncle.*—Length: 7.0 cm. Diameter: 0.40 cm. Angle: Upright. Strength: Sturdy, flexible. Color: RHS 146A.

Spathe:

*Appearance.*—Simple, hooded, cupped, enclosing spadix.

*Aspect.*—Upright.

*Shape.*—Elliptic.

*Apex.*—Cuspidate.

*Margin.*—Entire.
*Texture.*—Inside: Smooth, shiny. Outside: Smooth, glossy.
*Size.*—Length: 3.4 cm. Width: 1.3 cm (natural); 4.7 cm (flattened).
*Color.*—When opening: Front side: RHS 147C. Rear side: RHS 147B and RHS 146B spotted with RHS 146D. Fully opened: Front side: RHS 147C to RHS 147D. Rear side: RHS 147B to RHS 147C, RHS 146B spotted with RHS 146D. Fading to: RHS 200A to RHS 200B.

Spadix:
*Size.*—Length: 3.0 cm. Diameter (female zone): 0.85 cm. Diameter (male zone): 1.2 cm. Length of female zone: 0.4 cm. Length of male zone: 2.6 cm.
*Appearance.*—Columnar.
*Aspect.*—Upright.
*Shape.*—Columnar.
*Apex.*—Obtuse.
*Base.*—Obtuse.
*Margin.*—Pebbled.
*Color immature.*—Female zone: RHS 1C. Male zone: RHS 2D.
*Color mature.*—Female zone: RHS 10C. Male zone: RHS 8D.

Flower:
*Type.*—Simple.
*Quantity of female flowers per spadix.*—9.
*Quantity of male flowers per spadix.*—280.
*Shape of female.*—Ovate to elliptic.
*Shape of male.*—Obovate, inverted triangle.
*Size.*—Female width: 0.25 cm. Female height: 0.25 cm. Male width: 0.15 cm. Male height: 0.40 cm.

Reproductive organs:
*Anther color.*—RHS 8D.
*Pollen amount.*—None observed.
*Stigma color.*—RHS 10C.
*Ovary shape.*—RHS 145B.

Fruit and seed set: None observed.

Disease and insect resistance: Typical of *Aglaonema;* no particular susceptibility or resistance to pests or diseases noted.

COMPARISON WITH PARENTAL AND COMMERCIAL CULTIVARS

'TWYAG0013' differs from the female parent, an unknown individual plant of *A. rotundum* in that 'TWYAG0013' has leaves with pink blotches, while the female parent does not have leaves with pink blotches. In addition, 'TWYAG0013' has white to pinkish-white leaf venation, while the female parent has red to pinkish-red leaf venation. Also, 'TWYAG0013' has profuse suckering, while the female parent has moderate suckering.

'TWYAG0013' differs from the male parent, an unknown individual plant of *A. costatum* in that 'TWYAG0013' has leaves with pink blotches, while the male parent has leaves with white blotches. In addition, 'TWYAG0013' has an upright growth habit, while the male parent has a prostrate growth habit.

'TWYAG0013' differs from the commercial variety 'Donna Carmen' (unpatented) in that 'TWYAG0013' leaves are ovate, while 'Donna Carmen' has leaves that are oblong elliptical. In addition, 'TWYAG0013' has numerous blotches on the leaves that are evenly distributed, while 'Donna Carmen' has few blotches on the leaves that are sparsely distributed.

I claim:

1. A new and distinct cultivar of *Aglaonema* plant as shown and described herein.

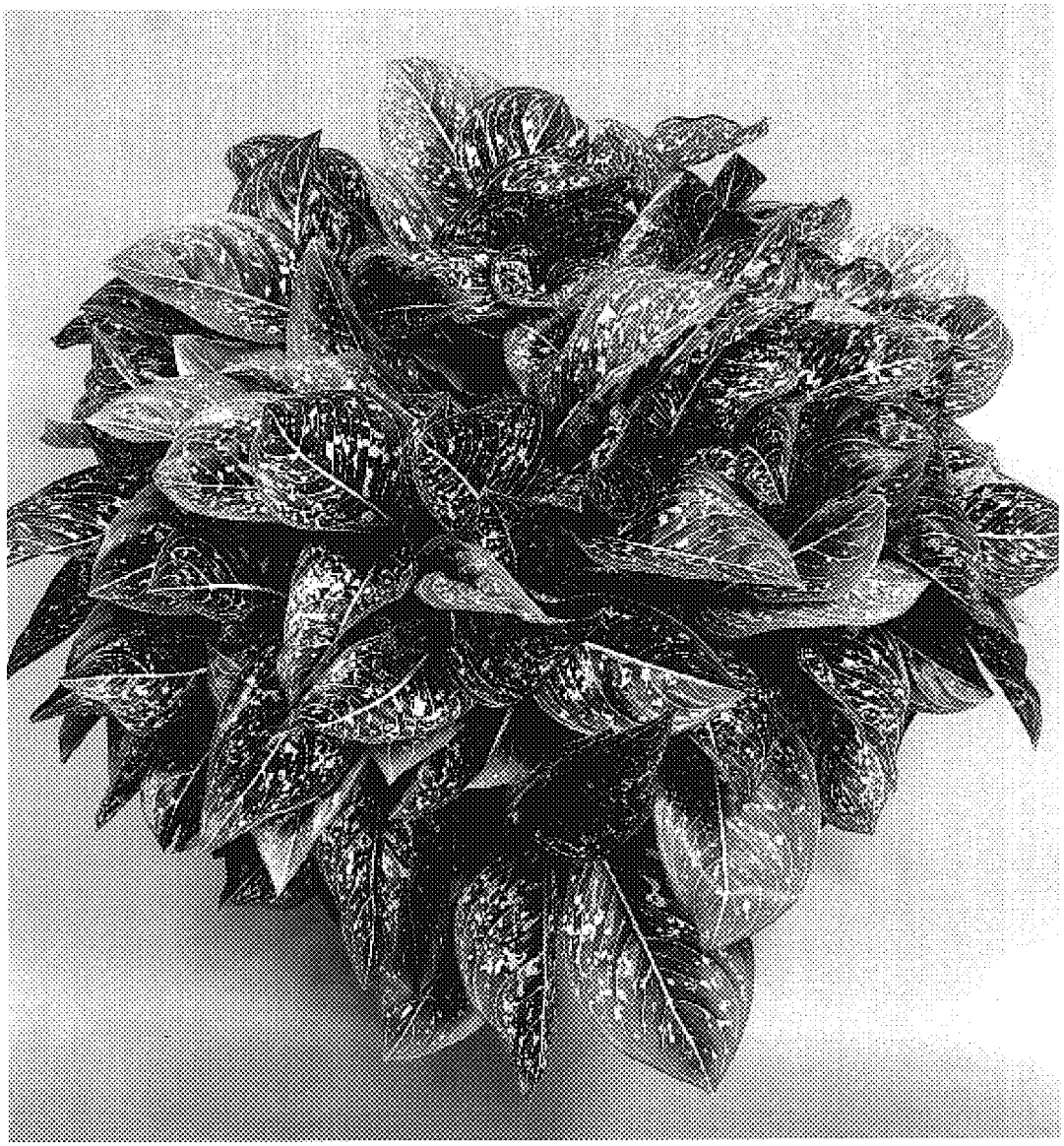

* * * * *